United States Patent [19]

Saran

[11] Patent Number: 4,990,674
[45] Date of Patent: Feb. 5, 1991

[54] SYNTHESIS OF ALIPHATIC AROMATIC PHOSPHINE OXIDES

[75] Inventor: Mohan S. Saran, Grand Island, N.Y.

[73] Assignee: Occidental Chemical Corporation, Niagara Falls, N.Y.

[21] Appl. No.: 366,120

[22] Filed: Jun. 14, 1989

[51] Int. Cl.$^5$ .............................................. C07F 9/02
[52] U.S. Cl. ...................................................... 568/14
[58] Field of Search ........................... 568/14; 562/808

[56] References Cited

U.S. PATENT DOCUMENTS

| | | | |
|---|---|---|---|
| 3,126,416 | 3/1964 | Willans | 564/14 |
| 3,833,662 | 9/1974 | Staendelve et al. | 568/14 |
| 3,931,196 | 1/1976 | Swan | 562/808 |
| 4,481,151 | 11/1984 | Kleiner | 562/816 |
| 4,632,995 | 12/1986 | Kleiner | 568/14 |
| 4,708,824 | 11/1987 | Kleiner | 562/808 |

FOREIGN PATENT DOCUMENTS 122587 10/1984 European Pat. Off. .

OTHER PUBLICATIONS

Hietkany, Chem Ber 117, 3400 (1984).
Nosolapoff, "Organophosphoras Compounds" pp. 138 & 139.
Kosolaloff et al., "Organic Phosphoral Compounds", vol. 1, pp. 19826, vol. 4 pp. 156-7.

*Primary Examiner*—Anton H. Sutto
*Attorney, Agent, or Firm*—James F. Tao; Richard D. Fuerle

[57] ABSTRACT

Disclosed is a method of making an aliphatic aromatic phosphine oxide by reacting an aliphatic aromatic phosphinic acid with a halogenating agent to produce a phosphoryl halide, reducing the phosphoryl halide to a phosphinous halide, hydrolyzing the phosphinous halide with water to produce a mixture of a phosphine and a phosphine oxide, determining how much phosphine is present in said mixture, and adding sufficient oxidizing agent to oxidize the phosphine in the mixture to the corresponding phosphine oxide. Octylphenyl phosphine oxide is preferred. The phosphine oxides are useful in making extractants for extracting actimides and lanthanides.

19 Claims, No Drawings

SYNTHESIS OF ALIPHATIC AROMATIC PHOSPHINE OXIDES

BACKGROUND OF INVENTION

This invention relates to the synthesis of aliphatic aromatic phosphine oxides by a five step process beginning with a phosphinic acid. In particular, it relates to the synthesis of octylphenyl phosphine oxide by that process.

Secondary phosphine oxides have a general formula:

Secondary phosphine oxides having one aliphatic group and one aromatic R group ("mixed" phosphine oxides) are of particular interest because they have been found to be very useful in making aliphatic aromatic N,N-dialkylcarbamoylmethyl phosphine oxides, which are useful in extracting lanthanides and actinides.

Phosphine oxides can be synthesized from phosphinic acids, which have the general formula:

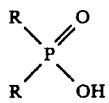

The synthesis of a phosphine oxide from the corresponding phosphinic acid, where both R groups are aliphatic or both R groups are aromatic, does not present any particular difficulties. But processes for synthesizing mixed phosphine oxides from mixed phosphinic acids are difficult and expensive.

One process is to react the mixed phosphinic acid with triethylamine and trichlorosilane in toluene to produce the mixed phosphine followed by oxidation to produce the mixed phosphine oxide (see E. P. Horwitz et al., Sol. Ext. and Ion Exch., 4, 449–494, 1986.):

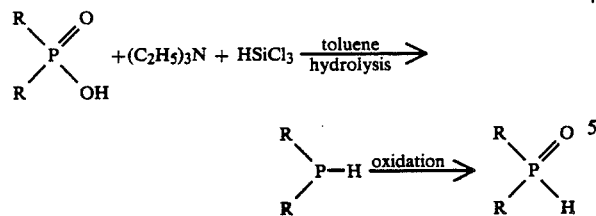

However, during the addition of trichlorosilane a voluminous, thick white precipitate is obtained and it is not possible to stir the reaction mixture unless large amounts of solvent are used. Difficulties are also encountered with stirring during the hydrolysis. As a result, yields are erratic and poor. Further work showed that the triethylamine can be eliminated, which reduced the stirring problems. However, if the toluene solution of the acid was below 20° C. during the addition of trichlorosilane, the reaction mixture would freeze into a sticky solid which made stirring extremely difficult. Yet the reaction could not be heated above 30° C. during trichlorosilane addition because unreacted trichlorosilane boils at about 31° to 32° C.

It is also possible to produce the mixed phosphine oxide from the mixed phosphinic acid by means of a Grignard reaction. However, the use of a Grignard reagent requires handling ether, which is highly flammable. Special equipment and facilities are required which are not economical for making small amounts of materials or for making materials that do not justify the expense.

SUMMARY OF THE INVENTION

I have discovered a safe, efficient, and effective way of producing mixed phosphine oxides from mixed phosphinic acids. Briefly, the process of this invention involves five steps: halogenating phosphinic acid to produce a phosphoryl halide, reducing the phosphoryl halide to a phosphinous halide, hydrolyzing the phosphinous halide to produce a mixture of a phosphine and a phosphine oxide, determining the amount of phosphine in the mixture, and adding sufficient oxidizing agent to oxidize the phosphine to the corresponding phosphine oxide. The process results in a high yield of relatively pure phosphine oxide and does not involve the use of ether. The stirring problems encountered in the previous process are also avoided.

DESCRIPTION OF THE INVENTION

In the process of this invention there are five required steps, plus additional optional steps. The starting material for the process of this invention is a aliphatic aromatic phosphinic acid having the general formula

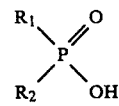

where $R_1$ is an aromatic group and $R_2$ is an aliphatic group. The aromatic group may be a single ring or a multiple ring aromatic group and the aromatic group can be substituted or unsubstituted. Examples of aromatic groups include xylyl, tolyl, benzyl, phenyl, halo substituted aromatics, and alkyl substituted aromatics. Carboxyl, hydroxyl, nitro, and amino substitutions should be avoided as they may react during one of the steps in the process. The preferred aromatic group is phenyl because those compounds make the best extractants.

The aliphatic group is preferably alkyl from $C_1$ to $C_{18}$ and is most preferably alkyl from $C_6$ to $C_{10}$ as those compounds make the best extractants. The most preferred aromatic aliphatic phosphinic acid is octylphenyl phosphinic acid because octylphenyl phosphine oxide can be used to make octylphenyl N,N-diisobutylcarbamoyl phosphine oxide which has been found to be a very effective extractant for actinides and lanthanides. Many mixed phosphinic acids are commercially available and those that are not commercially available can be prepared by well-known reactions.

In the first step of the process of this invention the phosphinic acid is reacted with a halogenating agent to produce a phosphoryl chloride:

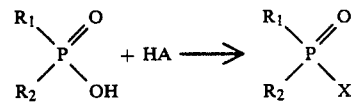

where "HA" is the halogenating agent and "X" is halogen. The halogenating agent is preferably a chlorinating agent as they are less expensive than fluorinating or brominating agents. Examples of halogenating agents include thionyl chloride, phosphorus pentachloride, phosphorus trichloride, and phosgene. Thionyl chloride is preferred as its reaction products are gaseous and are therefore easy to remove from the reaction mixture. No solvent is required for this reaction. The halogenating agent is preferably present in excess of stoichiometric to insure the complete reaction of the phosphinic acid. The phosphinic acid and the halogenating agent are heated, preferably to reflux. The reaction proceeds rapidly and is complete in a few minutes.

If the starting material, the phosphinic acid, is not pure, it is preferable to vacuum distill the phosphoryl chloride produced in the first step of the process of this invention to increase its purity. For example, if octylphenyl phosphinic acid is prepared by the free radical reaction of phenyl phosphinic acid with 1-octene using benzoyl peroxide as the initiator and ethanol as the solvent, vacuum distillation is desirable to purify the product before proceeding to the second step of the process of this invention.

In the second step of the process of this invention, the phosphoryl halide produced in the first step is reduced to a phosphinous halide:

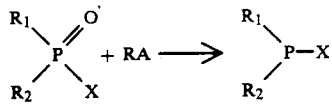

where "RA" is a reducing agent. Any potent reducing agent such as, for example, trichlorosilane or lithium aluminum hydride, can be used in this reaction. Trichlorosilane is preferred because it produces a high yield and it is easy to handle. It is preferable to slowly drip the trichlorosilane into the reaction mixture. After the addition is over, the reaction mixture is heated to between room temperature and about 75° C. The reaction can be followed by, for example, nuclear magnetic resonance (NMR) to determine when it is complete. The reaction mixture is then permitted to cool.

Before proceeding to the third step of the process of this invention, it is preferable to add a suitable organic solvent to the reaction mixture. Chlorinated solvents or hydrocarbons are suitable for this purpose. The preferred solvent is methylene chloride because it keeps the temperature of the reaction mixture below about 38° C., preventing the oxidation of the phosphine oxide back to phosphinic acid during H₂O₂ oxidation of the co-produced octyl phenyl phosphine (in the fifth step of the process).

In the third step of the process of this invention, the phosphinous halide is hydrolyzed with water to produce a mixture of a phosphine and a phosphine oxide:

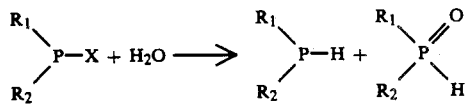

This reaction is highly exothermic so the water should be added slowly. A siliceous precipitate is usually produced in this reaction which can be removed by filtration. Alternatively, an aqueous solution of sodium hydroxide can be added, which will dissolve the precipitate and form two phases.

In the fourth step of the process of this invention, the amount of the phosphine present in the mixture is determined. This determination can be made by NMR or other methods, but it is conveniently made by gas chromatograph (GC).

In the fifth step of the process of this invention, sufficient oxidizing agent is added to oxidize the phosphine present in the mixture to the corresponding phosphine oxide:

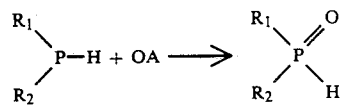

where "OA" is the oxidizing agent. While a number of oxidizing agents, such as hydrogen peroxide, air, oxygen, or potassium permanganate, can be used, the preferred oxidizing agent is hydrogen peroxide because its product is water. Care must be taken not to add too much oxidizing agent as that may result in the oxidation of the phosphine oxide back to the phosphinic acid.

If desired, dilute sodium hydroxide can be added to the product mixture to form salts with any organophosphoric acids that may be present, thereby removing them to the aqueous phase. However, if the product is purified by, for example, wipe film distillation, it is not necessary to add the dilute sodium hydroxide. The resulting phosphine oxides are useful in making extractants. See, for example, U.S. Pat. No. 4,396,556, herein incorporated by reference.

The following example further illustrates this invention.

EXAMPLE

The starting material, octylphenyl phosphinic acid, was prepared by reacting 504 g. phenyl phosphinic acid with 426 g. 1-octene, using 24 g. benzoyl peroxide as a catalyst in refluxing ethanol (79°–81° C.) for thirteen hours. Alcohol was stripped off using a water-pump vacuum. Octylphenyl phosphoryl chloride (1001 g.) was produced from the octylphenyl phosphoric acid by adding 528 g. thionyl chloride to the stirred mixture over a twenty minute period. The reaction mixture was then refluxed for 4½ hours at 74° C. Dissolved gasses and any excess thionyl chloride were stripped off under vacuum.

Octylphenyl phosphinous chloride was made from the octylphenyl phosphoryl chloride by the addition of 436.8 g. trichlorosilane over a twenty minute period. The reaction mixture was then heated to 75° C. for two hours. After cooling to 0° C., 1025 ml. methylene chloride was added and the well-stirred mixture was slowly and carefully hydrolyzed with 550 ml. water to produce a mixture of octylphenyl phosphine and octylphenyl phosphine oxide. The water was added slowly and the stirring was efficient. The solids were then dissolved by adding 450 ml. of a 50% caustic solution. The methylene chloride layer was separated and analyzed by (GC). The concentration of octylphenyl phosphine in the mixture was determined to be 26.6 mole %. The octylphenyl phosphine in the mixture was oxidized by adding the calculated amount (96 g.) of 30% hydrogen peroxide to the stirred methylene chloride solution of this product, keeping the temperature below 40° C. The organic layer was separated, dried over anhydrous magnesium sulfate, and stripped of methylene chloride. The product was purified by wipe film distillation using a condenser temperature of 110° C. and a wall temperature of 165°-170° C. at a vacuum of 0.3 mm Hg. The octylphenyl phosphine oxide product (347 g., 72.9% yield) was obtained as a colorless liquid.

I claim:

1. A method of making a phosphine oxide having the general formula

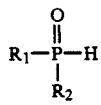

where $R_1$ is aromatic and $R_2$ is aliphatic, comprising
   (1) reacting the phosphinic acid

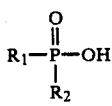

with a halogenating agent to produce the phosphoryl halide

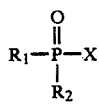

where X is halogen;
   (2) reducing said phosphoryl halide to the phosphinous halide

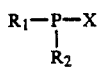

using as the reducing agent about one mole of trichlorosilane per mole of said phosphoryl halide;
   (3) hydrolyzing said phosphinous halide with water to produce the phosphine oxide

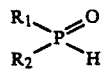

as the major product and the phosphine

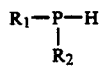

the minor product; and
   (4) adding sufficient oxidizing agent to oxidize said phosphine to the corresponding phosphine oxide.

2. A method according to claim 1 wherein $R_2$ is alkyl from $C_1$ to $C_{18}$.

3. A method according to claim 2 wherein $R_2$ is alkyl from $C_6$ to $C_{10}$.

4. A method according to claim 3 where $R_1$ is phenyl and $R_2$ is octyl.

5. A method according to claim 1 wherein said halogenating agent is a chlorinating agent.

6. A method according to claim 5 wherein said chlorinating agent is thionyl chloride.

7. A method according to claim 1 wherein said oxidizing agent is hydrogen peroxide.

8. A method according to claim 1 wherein the amount of said oxidizing agent is about one mole per mole of said phosphine.

9. A method of making octylphenyl phosphine oxide from octylphenyl phosphoric acid comprising:
   (1) heating said octylphenyl phosphoric acid with thionyl chloride to produce octylphenyl phosphoryl chloride;
   reducing said octylphenyl phosphoryl chloride with about one mole of trichlorosilane per mole of said octylphenyl phosphoryl chloride to produce octylphenyl phosphinous chloride;
   (3) hydrolyzing said octylphenyl phosphinous chloride with water to produce a mixture containing octylphenyl phosphine oxide as the major product and octylphenyl phosphine as the minor product; and
   (4) adding hydrogen peroxide in an amount sufficient to oxidize said octylphenyl phosphine to octylphenyl phosphine oxide.

10. A method according to claim 9 including the additional step, between steps (1) and (2), of vacuum distilling said octylphenyl phosphoryl chloride.

11. A method according to claim 9 including the additional step, between steps (2) and (3), of adding a chlorinated or hydrocarbon solvent, whereby an aqueous phase and an organic phase are formed in step (3).

12. A method according to claim 11 including the additional step, between steps (3) and (4), of adding sodium hydroxide to dissolve precipitates in said aqueous phase.

13. A method according to claim 9 wherein the amount of said hydrogen peroxide is about one mole per mole of said octylphenyl phosphine.

14. A method of making a phosphine oxide having the general formula

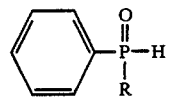

where R is alkyl from $C_1$ and $C_{18}$, comprising
   (1) reacting the phosphinic acid

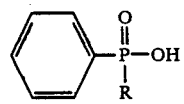

with a halogenating agent to produce the phosphoryl halide

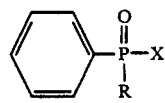

where X is halogen,
   (2) reducing said phosphoryl halide to the phosphinous halide

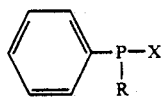

using about one mole of trichlorosilane as the reducing agent per mole of said phosphoryl halide
(3) hydrolyzing said phosphinous halide with water to produce the
phosphine oxide

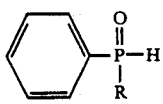

as the major product and the phosphine

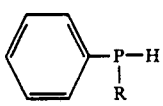

as the minor product; and
(4) oxidizing said phosphine to said phosphine oxide using about one mole of an oxidizing agent per mole of said phosphine.

15. A method according to claim 14 wherein, prior to step (3), methylene chloride is added to the reaction mixture.

16. A method according to claim 14 wherein said halogenating agent is thionyl chloride, said oxidizing agent is hydrogen peroxide, and said reducing agent is trichlorosilane.

17. A method according to claim 14 including the additional step, between steps (2) and (3), of adding a chlorinated or hydrocarbon solvent, whereby an aqueous phase and an organic phase are formed in step (3).

18. A method of making the phosphine oxide

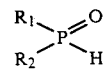

where $R_1$ is aromatic and $R_2$ is aliphatic, comprising:
(a) reducing the phosphoryl halide

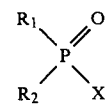

where X is halide, to the phosphinous halide

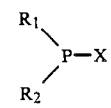

using about one mole of trichlorosilane per mole of phosphoryl halide; and
(b) hydrolyzing said phosphinous halide with water to produce said phosphine oxide.

19. A method according to claim 18 where X is Cl.

* * * * *

UNITED STATES PATENT AND TRADEMARK OFFICE
CERTIFICATE OF CORRECTION

PATENT NO.   :   4,990,674

DATED        :   February 5, 1991

INVENTOR(S)  :   Mohan S. Saran

It is certified that error appears in the above-identified patent and that said Letters Patent is hereby corrected as shown below:

On the title page, item [57]:
Abstract, line 12, delete "actimides" and substitute -- actinides --.

Column 5, line 58, before "the minor" insert -- as --.

Column 6, line 13, before "reducing" insert -- (2) --.

Signed and Sealed this

First Day of October, 1991

Attest:

HARRY F. MANBECK, JR.

*Attesting Officer*    *Commissioner of Patents and Trademarks*